United States Patent [19]

Cameron et al.

[11] Patent Number: 4,994,447
[45] Date of Patent: Feb. 19, 1991

[54] METHOD FOR CONTROLLING PHYTOPATHOGENIC FUNGI USING BRANCHED AMINOALKANEPHOSPHONIC ACIDS

[75] Inventors: David G. Cameron, Stockholm, Sweden; Harry R. Hudson, London, England; Inger Lagerlund, Bromma, Sweden; Max Pianka, Wembley Park, England

[73] Assignee: KenoGard AB, Sweden

[21] Appl. No.: 373,002

[22] Filed: Jun. 29, 1989

Related U.S. Application Data

[60] Division of Ser. No. 207,921, Jun. 10, 1988, Pat. No. 4,888,330, which is a continuation of Ser. No. 851,211, Apr. 14, 1986, abandoned, which is a continuation-in-part of Ser. No. 695,227, Jan. 28, 1985, abandoned.

[30] Foreign Application Priority Data

Jan. 30, 1984 [SE] Sweden ............................ 8400458

[51] Int. Cl.$^5$ .................... A01N 57/00; A01N 57/26
[52] U.S. Cl. ..................................... 514/114; 514/76
[58] Field of Search ............................. 514/76, 114

[56] References Cited

U.S. PATENT DOCUMENTS 3,764,677 10/1973 Kerst et al. .................... 514/114
4,147,780 4/1979 Dingwall et al. ............... 514/114
4,469,686 9/1984 Andrews ........................ 514/92

FOREIGN PATENT DOCUMENTS 2315886 11/1979 Fed. Rep. of Germany .
2269862 12/1975 France .
2461725 3/1981 France .
697519 11/1979 U.S.S.R. .

OTHER PUBLICATIONS

Soviet Reference No. 557,579, dated Aug. 7, 1978, (English Language Abstract only).
Soviet Reference No. 697,519, dated Nov. 15, 1979, (English Language Abstract only).
English Language Translation of Soviet Reference No. 697,519.
*Chemical Abstracts:* A. I. Ryzhkov et al., vol. 49, No. 3403-3404a, (1955).
*Chemical Abstracts:* A. J. Lacoste et al., vol. 82, No. 165298j, (1975).
*Chemical Abstracts:* A. K. Glowiak et al., vol. 88, No. 152713q, (1978).
*Chemical Abstracts:* A. L. Azerbaev et al., vol. 90, No. 1686y, (1979).
*Chemical Abstracts:* A. M. Bakuniak et al., vol. 99, No. 189788w, (1983).
Siepak et al., *Pharmazie,* 36, H 11, pp. 782-783, (1981).
Glowiak et al., *Tetrahedron Letters,* No. 45, pp. 3965-3968, (1977).
Bakuniak et al., *J. Environ. Sci. Health,* B18 (4&5), pp. 485-496, (1983).
Ryzhkov et al., Doklady Akademii Nauk SSSR, vol. XCVIII, No. 5, (1954), (entire English language translation).

*Primary Examiner*—Allen J. Robinson
*Attorney, Agent, or Firm*—Lowe, Price, LeBlanc, Becker & Shur

[57] ABSTRACT

Branched aminoalkanephosphonic acids, i.e. compounds containing at least one alkyl substituent in the aposition to the phosphonic acid group are used for controlling phytopathogenic fungi by applying an effective amount of the compound to seed or foliage.

24 Claims, No Drawings

METHOD FOR CONTROLLING PHYTOPATHOGENIC FUNGI USING BRANCHED AMINOALKANEPHOSPHONIC ACIDS

The present application is a divisional application of Application Ser. No. 07/207,921 filed June 10, 1988, now U.S. Pat. No. 4,888,330, which is a continuation of Application Ser. No. 06/851,211 filed Apr. 14, 1986, now abandoned, which is a continuation-in-part of Application Ser. No. 06/695,227 filed Jan. 28, 1985, now abandoned.

The present invention relates to a method for killing or inhibiting the growth of phytopathogenic fungi using certain branched aminoalkanephosphonic acids. The compounds used according the method have been found to be particularly suitable for control of fungal diseases in plants.

Various biological effects of different aminoalkanephosphonic acid compounds are previously known. From the U.S. Pat. No. 3,764,677 fungicidal effect against phytopathogenic fungi is known for specific esters of a straight chain aminoalkanephosphonic acid, namely diethyl betaaminoethylphosphonate. Allyl and propynyl esters of a straight chain aminoalkanephosphonic acid, aminomethylphosphonic acid, have also been disclosed as having such an effect. The USSR patent No. 697519 discloses a process for the preparation of such branched aminoalkanephosphonic acids as are used according to the present invention. In the USSR patent it is alleged that the branched aminoalkanephosphonic acids find application as corrosion inhibitors, complexones, antioxidants, and also as insecticides or fungicides.

According to the present invention it has been found that certain branched aminoalkanephosphonic acids are especially useful as fungicides for phytopathogenic fungi and can thus be used in agriculture and horticulture. Branched aminoalkanephosphonic acids herein refers to aminoalkanephosphonic acids which have at least one alkyl substituent in the α-position to the phosphonic acid group.

According to the present method for controlling phytopathogenic fungi the aminoalkanephosphonic acids are used as seed-dressing agents or as foliar sprays.

The branched aminoalkanephosphonic acids used in the method of the invention have the general formula

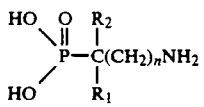

wherein n is 0 or 1; $R_1$ is an alkyl group having 1 to 12 carbon atoms and $R_2$ is hydrogen or an alkyl group having 1 to 12 carbon atoms.

Branched aminoalkanephosphonic acids used according to the present invention can eg be prepared by condensation of alkylcarbamates with aldehydes and triphenylphosphite, as described in Tetrahedron Letters No. 32, 1977, pages 2823 to 2824. Salts of the acids can be prepared in per se known manners, eg as shown in the examples.

The important feature of the compounds used is the α-substitution to the phosphonic acid group by one or two alkyl groups. The number of carbon atoms in these alkyl groups, $R_1$ and $R_2$, should suitably not exceed 8, and preferably not exceed 5. If two branches are present the total number of carbon atoms should suitably not exceed 8 and preferably not exceed 5. Thus the preferred compounds are such containing short branches, and particularly such with one short branch. Compounds wherein n is 0 are preferred. It has been found that particularly good effect is obtained with the aminoalkanephosphonic acid 1-aminopropanephosphonic acid, wherein the branch thus is an ethyl group. The compounds can be in the form of their acid addition salts acceptable to the use. Here salts of organic acids can be used but the acid addition salts are preferably salts of mineral acids such as hydrochloric acid, sulphuric acid and phosphoric acid etc.

In the present method for controlling phytopathogenic fungi the compounds are used as seed-dressing agents or as foliar fungicides, preferably as seed-dressing agents, and they are hereby used in amounts effective to kill or inhibit the growth of the fungi in question, the dosage being decided from desired protection, material to be treated, treatment method etc.

The compounds are soluble in water, the solubility varies depending on structure and pH, and they can generally be used in the form of water based formulations. They can also be used in formulations with conventional carriers and diluents. They can be included in solid formulations such as powders, granules and pellets comprising carriers such as talcum, clay, silicates etc. Liquid preparations comprise diluents, e.g. water and/or solvents such as ethanol, ethyl acetate, glycols, vegetable oils, dimethyl formamide, N-methylpyrrolidone etc. For formulation of the present active compounds conventional additives and adjuvants can be incorporated into powder, dust and liquid formulations. Examples of such are surface active agents, wetting agents, stabilizers etc. The active compounds of the present invention are also compatible with other fungicidal agents and agents of other biocidal activity, such as insecticides, and can be used in combination with such agents if so desired. The concentration of the active substance in formulations as above is generally between 1 and 60 percent by weight.

The compounds have shown an excellent effect against fungi of the genus Drechslera, against *Septoria nodorum, Ustilago hordei* and other crop-attacking fungi and they can thus advantageously be used as seed-dressing agents.

Although the invention above has been described in the terms of the specific branched aminoalkanephosphonic acids it falls within the scope of the invention that fungicidally active salts of the acids are used for the control of phytopathogenic fungi in the use as seed-dressing agents or foliar sprays. Salts here refer to metal salts, ammonium salts, salts of amines and quaternary ammonium compounds.

Metal salts include e.g. salts of alkali metals, alkaline earth metals, copper, cobalt, zinc, tin and aluminium. Salts of amines include salts of primary, secondary and tertiary amines, which are aromatic, such as e.g. salts of aniline and alpha-naphtyl-amine, aliphatic or cycloaliphatic containing higher or lower aliphatic groups, and further include salts of cyclic amines such as e.g. morpholine and pyrrolidine and related compounds. Amines include mono-, di- and polyamines. Quaternary ammonium compounds which can form salts with the branched aminoalkanephosphonic acids include short chain quaternary compounds, with 1 to 5 carbon atoms, such as e.g. tetramethyl ammonium compounds and tetrabutyl ammonium compounds, and quaternary ammonium compounds containing one or more hydrophobic groups, the other groups being for example shorter alkyl or hydroxyalkyl groups. These quaternary ammonium compounds can for example be alkyl trimethyl ammonium compounds, dimethyl dialkyl ammonium compounds, benzyl dimethyl alkyl ammonium compounds, wherein the alkyl chain contains from 6 to 20 carbon atoms, and quaternary ammonium compounds containing corresponding alkylene groups.

The invention is further illustrated in the following examples which, however, are not intended to limit the same. Parts and percent relate to parts by weight and percent by weight, unless otherwise stated.

EXAMPLE 1

Preparation of 1-Aminopropanephosphonic Acid

Ethyl carbamate (4.45 g), triphenyl phosphite (15.5 g) and propanal (4.06 g) were heated under reflux (1 hour) with acetic acid (10 ml). Concentrated hydrochloric acid (50 ml) was added and the mixture was heated under reflux (6 h) and then allowed to cool. The aqueous phase was separated, washed with benzene (20 ml) and then evaporated to dryness. The residue was dissolved in methanol (40 ml) and propylene oxide was added until the pH was 6. The crude phosphonic acid was filtered off and recrystallised from water/methanol to yield a fine white crystalline solid (4.2 g, 60.4%) with a melting point of 264°-6° C.

EXAMPLE 2

Preparation of the di-(1-Aminopropanephosphonic Acid) Salt of 1,6-Diaminohexane 1-aminopropanephosphonic acid (3.95 g, 284 mmol) and 1,6-diaminohexane (1.65 g, 142 mmol) were dissolved in water (40 ml) and the water was then distilled off. Ethanol (50 ml) was then added and also then distilled off. The residue was dried in a vacuum oven at 50° C. (4 h) to yield the above salt as a fine crystalline solid (5.5 g, 98.2%) with a melting point of 244°-50° C.

EXAMPLE 3

Preparation of the Tetrabutylammonium Salt of 1-Aminopropanephosphonic Acid

To 1-aminopropanephosphonic acid (2.91 g, 209 mmol) and tetrabutylammonium bromide (6.74 g, 209 mmol) was added water (50 ml), propylene oxide (20 ml) and water (50 ml). The resultant solution was then heated at 50° C. (½ h) and allowed to cool. Evaporation of the volatile components, drying in a vacuum oven at 50° C. (6 h) and further drying over silica gel (4 days) yields the required compound as a colourless, viscous oil (7.5 g, 94.2%).

EXAMPLE 4

Preparation of Copper Salt of 1-Aminopropanephosphonic Acid 1-aminopropanephosphonic acid (5.251 g, 378 mmol) and copper acetate monohydrate (7.612 g, 378 mmol) were dissolved in water (50 ml) and the water was distilled off. Water (50 ml) was added to the residue, and the solid was filtered off, washed with acetone (2×20 ml) and dried in a vacuum oven at 60° C. (3 h) to yield the required copper salt as a blue-green powder (6.9 g, 90.2%).

EXAMPLE 5

Preparation of Morpholine Salt of 1-Aminopropanephosphonic Acid 1-aminopropanephosphonic acid (4.01 g, 288 mmol) and morpholine (5.02 g, 577 mmol) were dissolved in water (20 ml) and ethanol (20 ml) was added. The solvents and excess amine were evaporated off, acetone (50 ml) was added and the solid was filtered off, washed with acetone (50 ml) and then dried in a vacuum oven at 60° C. (4 h) to yield the morpholine salt of 1-aminopropanephosphonic acid (5.5 g, 84.4%) with a melting point of 62°-64° C.

Similarly prepared were the salts of the following amines, yield and melting point are given in brackets.
3-hydroxypropylamine (98.8%, 156°-60° C.)
cyclohexylamine (96.3%, 260°-64° C.)
pyrrolidone (86.5%, 76°-78° C.)
diethylamine (95.5%, 84°-88° C.)
piperazine (87.4%, 98°-108° C.)
hexylamine (94.3%, 266°-68° C.)
N,N-dimethylethanolamine (89.6%, 260°-64° C.)

All the salts prepared according to examples 2 to 5 were characterized and identified by $^{13}C$ and $^{1}H$ nuclear magnetic resonance spectroscopy.

EXAMPLE 6

The fungicidal activity of the following compounds was tested:

$$(HO)_2P(=O)-C(R_1)(R_2)-NH_2$$

| | $R_1$ | $R_2$ |
|---|---|---|
| (1) | $CH_3$ | H |
| (2) | $C_2H_5$ | H |
| (3) | $CH(CH_3)_2$ | H |
| (4) | $C_7H_{15}$ | H |
| (5) | $CH_3$ | $CH_3$ |
| (6) | $C_2H_5$ | $C_2H_5$ |
| (7) | $CH(CH_3)_2$ | $CH_3$ |
| (8) | $C_3H_7$ | H |
| (9) | $C_4H_9$ | H |
| (10) | $C_5H_{11}$ | H |
| (11) | $C_2H_5$ | H as potassium salt |
| (12) | $C_2H_5$ | H as copper (II) salt |

The activity of the substances was examined using a mycelial growth inhibition test on agar according to the following method.

The substances were dissolved in sterilized potato dextrose agar (PDA) to give a concentration of 500 ppm. The mixtures were then poured onto standard petri dishes of 9 cm diameter. An agar plug (5 mm diameter) with lively growing mycelia (cultivated on PDA) was placed in the center of each petri dish. After incubation at 28° C. for 1 to 3 weeks, depending on the growth rate of the respective fungus, the growth diameter was measured and compared with that of untreated dishes.

The effect was tested against *Drechslera sativa* for some compounds and against *Drechslera teres* for some.

In the table the results are shown by classifying the compounds according to the following scale:
0=0-25% inhibition of growth
1=26-50% inhibition of growth
2=51-75% inhibition of growth 3 = 76-100% inhibition of growth

TABLE

| Compound | Control of *D. sativa* |
| --- | --- |
| 1 | 3 |
| 2 | 3 |
| 3 | 3 |
| 4 | 3 |
| 5 | 3 |
| 6 | 2 |
| 7 | 3 |

| | Control of *D. teres* |
| --- | --- |
| 8 | 3 |
| 9 | 3 |
| 10 | 2 |
| 11 | 3 |
| 12 | 2 |

In the same manner as described above the effect of some of the compounds at a dosage of 500 ppm was tested against *Fusarium culmorum*. The tested compounds were numbers (8), (9) and (10) and they gave a control of 3, 3 and 2 respectively.

Also in the same manner some salts of compound 2 were tested against *Rhizoctonia solani* at a dosage of 300 ppm. The salts were the following: (a) salt of diethyl amine, (b) salt of cyclohexylamine, (c) salt of morpholine and (d) salt of pyrrolidine, they all gave a control of 3.

EXAMPLE 7

The effect of some compounds according to the invention against *Drechslera teres* was examined by in vivo tests.

The tests were made according to the osmos-method. This method involves placing dressed seed on filter papers moistened with a buffered sugar solution. The filter papers are then placed in covered transparent plastic dishes. The dishes are placed in a thermostat-controlled cabinet which maintains a temperature of 22° C. and gives alternating periods of 12 hours light and 12 hours darkness.

The examination was carried out after one week. Seed that has survived shows grown hyphae which form a blot, but the seed has not germinated due to the osmotic pressure. Seed with living fungi is identified by a colour test. The method is rather severe and all seeds with living fungi are counted, even seed with a very slight infection, which would not have been seen in a growing plant. The results of the test are given as percent control, where the infection of untreated seed, for each test, is set to 100%.

The following salts of 1-aminopropanephosphonic acid were tested at a dosage of 2 ml aqueous solution (20% active ingredient) per kg seed:
(a) cyclohexylamine salt
(b) hydroxypropylamine salt
(c) morpholine salt
(d) pyrrolidine salt
(e) diethylamine salt The results were as follows:
(a) 64
(b) 26
(c) 74
(d) 92
(e) 47

EXAMPLE 8

In this example the effect of 1-aminopropanephosphonic acid as a foliar fungicide was examined.

Barley of variety Agneta (6-row barley) was cultivated in standard soil to stage 12 (decimal code for growth stages) during 9 days. The growth climate was 10000 Lux, lighting for 8 hours and a temperature of between 15° and 20° C. Spores of powdery mildew, *Erysiphe graminis* f. sp. *hordei* from infected plants were shaken over uninfected plants. Incubation was carried out in a moist-chamber with 100% humidity for 24 hours at 17° C. The plants were then moved back to a green house. Infection started to show after 5 days and the results were recorded after 8 days.

The test was a preventive test were the plants were sprayed with the active compound before infection. The plants, 10 for each pot, were sprayed with an aqueous solution containing 500 ppm of the aminophosphonic acid. The solution contained a wetting agent. 6 pots, i.e. 60 plants, were used for the test. As a comparison a commercial product (Forbel 750 g a.i./ha) was used in the same manner and a comparison was also made with untreated plants. The number of powdery mildew pustles on the plants after the incubation period was counted and the results were as follows: untreated 14 (=0% effect), treated with substance according to the invention 3 (75% effect), treated with commercial product 0 (=100% effect).

EXAMPLE 9

In these field tests the effect of 1-aminopropanephosphonic acid against a number of different fungi was tested.

1. *Septoria nodorum*

(Leaf and Glume Blotch)

Material and method: Winter wheat, variety Holme, with a heavy natural infection of the fungus *S. nodorum* was used in the trial. The wheat seed was weighed and treated with a formulation containing the compound at a dosage rate of 2 ml per kg seed (20% active ingredient). Seed-treatment was made in a seed-treating machine. The seed was sown in the autumn in randomised block-design trials (1.3 × 10 m per plot and 4 replicates).

When the plants had 2-3 leaves the plants were dug up on 2 meters per plot and the attack on the coleoptiles was assessed.

2. *Ustilago hordei*

(Covered Smut of Barley)

Material and method: Barley, variety Birka, was infected with 4 g of smut spores per kilo of seed. The barley seed was weighed and treated with 2 ml of the formulation (20% active ingredient) per kilo seed. The seed was sown in the spring in randomised block-design trials.

The number of diseased ears was assessed on an area of 9.4–11.4 square meters per plot.

3. *Drechslera teres*

(Net Blotch)

Material and method: Barley seed of the variety Tellus, with a heavy natural infection of the fungus *D. teres* was utilised in the trials. The seed was treated as described above and sown in the spring.

At the 2-leaf stage assessment was made of plants with primary attacks on the first leaf.

The attacks are given in figures relative to the attacks on untreated seed (=100% for untreated). The efficacy of the compound is given as percent control (=0% for untreated) and the results are shown in the table. When trials were carried out at two different sites, the results are given separately.

In further field tests the effect of 1-aminopropanephosphonic acid against a number of other fungi was examined.

4. *Tilletia caries*

(Stinking Smut of Winter Wheat)

Material and method: Winter wheat, variety Holme, was infected with 5 g of smut spores per kilo of seed. The wheat seed was weighed and treated with 2 ml of the composition (20% active ingredient) per kg seed. Seed treatment was made in a seed treating machine. The seed was sown in autumn in randomised block-design trials (2 m × 16 m per plot and 4 replicates).

The number of diseased ears was counted on area of 10 square meters per plot.

5. *Drechslera graminea*

(Barley Leaf Stripe)

Material and method: Barley seed of the variety Agneta, with a heavy natural infection of the fungus *D. graminea* was utilised in these trials. The seed was treated as described above, with 2 ml composition per kg seed, and sown in the spring.

At the 5–6 leaf stage (Feekes-Large no. 6, Decimal code no. 31–32) the number of diseased plants per square meter was counted.

6. *Drechslera avenae*

(Net Blotch of Oat)

Material and method: Oat seed, variety Selma, with a natural infection of the fungus *D. avenae* was utilised in these trials. The seed was treated at a dosage rate of 2 ml per kg seed (20% a.i.).

At the 2-leaf stage the number of diseased plants per square meter was counted.

7. *Ustilago avenae*

(Loose Smut of Oat)

Material and method: Oat seed, variety Hedvig, was infected with 3 g of smut spores per 3 liters of water (wet-infection with vacuum). The infected seed was dried in thin layers in room temperature, until the water content was about 15%. The dry, infected seed was treated with 2 ml of the composition (20% a.i.) per kg seed in a seed-dressing machine.

The treated seed was sown in spring in randomised block-design trials (1.35 m × 8 m per plot and 4 replicates). The number of diseased ears was counted and the result given as the number per 3 square meters.

The results for these field trials are given in the table in the same manner as stated earlier.

TABLE

| Fungus | Attack | Control |
|---|---|---|
| *Septoria nodorum* Treated | 27 | 73 |
| *Ustilago hordei* | | |
| Trial site I Treated | 22 | 78 |
| Trial site II Treated | 28 | 72 |
| *Drechslera teres* | | |
| Trial site I Treated | 0 | 100 |
| Trial site II Treated | 0.3 | 99.7 |
| *Tilletia caries* Treated | 18 | 82 |
| *Drechslera graminea* | | |
| Trial site 1 Treated | 4 | 96 |
| Trial site II Treated | 1 | 99 |
| *Drechslera avenae* | | |
| Trial site I Treated | 0 | 100 |
| Trial site II Treated | 1 | 99 |
| *Ustilago avenae* | | |
| Trial site I Treated | 4 | 96 |
| Trial site II Treated | 5 | 95 |

In field tests, as above, the effect of a straight chain aminoalkanephosphonic acid with the same number of carbon atoms, 3-aminopropanephosphonic acid, against *Drechslera teres* and *Drechslera avenae* was examined as a comparison. The control of infection obtained by this compound was 28 and 37 percent respectively.

EXAMPLE 10

The effect of salts of 1-aminopropanephosphonic acid against *D. graminae* was investigated and the test was carried out as follows:

Seed treated with the salts, in aqueous formulations at a dosage of 0.4 g a.i. per kg seed, were sown in dishes containing moist earth mixed with gravel. The dishes were kept in a cold place (+6° C.) for 10 to 12 days. They were then kept at room temperature and illuminated until they had reached the 2–3 leaves stage. The test was then evaluated. The number of germinated plants and plants with characteristic spots on coleoptile, leaves and roots respectively were counted. The percent attack for each treatment is compared with that for untreated seed. The attack for untreated seed is set to 100% and the seed dressing effect given below is in percent relative to this:

Salt of 1-Aminopropanephosphonic Acid/% Effect (a) potassium salt, 97%
(b) copper (II) salt, 98%
(c) cyclohexylamine salt, 100%
(d) 3-hydroxypropylamine salt, 100%
(e) piperazine salt (bis-acid salt of piperazine), 98%
(f) hexamethylenediamine salt (bis-acid salt), 100%
(g) hexylamine salt, 98%
(h) dimethyl ethanolamine salt, 100%

Similarly the effect of several salts against *Septoria nodorum* was investigated. Seeds treated with the salts, in aqueous formulations at a dosage of 0.4 g a.i. per kg seed, were sown in soil contained in bowls of 20 cm diameter (50 kernels/bowl). The bowls were then kept in a growing chamber at +6° C. for 10 to 12 days and then moved into a climate cabinet. The conditions in the climate cabinet were: temperature 20° C. in the day, 10° to 13° C. at night with a 16 h day and an 8 h night. The disease was assessed when the plants had reached the 2½ leaf stage. The level of disease was compared to a control, whose level of infection was set to 100%.

SALT OF 1-Aminopropanephosphonic Acid/% Effect (a) potassium salt, 100%
(b) copper salt, 94%
(c) diethylamine salt, 100%
(d) cyclohexylamine salt, 100%
(e) morpholine salt, 94%
(f) pyrrolidine salt, 100%
(g) piperazine salt (bis-acid salt), 100%
(h) hexamethylenediamine salt (bis-acid salt), 100%
(i) hexylamine salt, 94%
(j) 2-aminobutane salt, 100%
(h) isopropylamine salt, 94%
(l) tetrabutylammonium salt, 94%
(m) hydrochloric acid addition salt, 100%

EXAMPLE 11

In this test of comparison was made between the diethyl betaaminoethylphosphonate according to the U.S. Pat. No. 3,764,677 (Kerst) and 1-aminopropanephosphonic acid. The tests were made according to the osmos-method as described in Example 7. The effect of the compounds were tested against *Drechslera teres* at adosage of 0.4 g a.i./kg of seed.

The diethyl betaaminoethylphosphonate gave an effect of 3%, while the 1-aminopropanephosphonic acid according to the present invention gave an effect of 50%.

EXAMPLE 12

The following salts of 1-aminopropanephosphonic acid were evaluated in field trials against a number of different fungi:
Salt (a)=monopotassium salt
Salt (b)=copper salt
Salt (c)=hexamethylene diamine salt (bis-acid salt)
Salt (d)=isopropylamine salt
Salt (e)=2-aminobutane salt The methods for treatment of seed and evaluation of effect were in accordance with those disclosed in Example 9 for the respective types of seeds and fungi. Variety of seed and dosage were as set out below. All seed treatments were made with aqueous formulations of the salts.

1. *Drechslera teres*

(Net Blotch on Barley)

Barley seed of the variety Gunilla. Dosage 200 ml per 100 kg seed of formulations containing 150 g a.i. per liter.

2. *Drechslera graminae*

(Barley Leaf Stripe)

Barley seed of the variety Agneta Dosage 200 ml per 100 kg seed of formulations containing 150 g a.i. per liter.

3. *Drechslera avenae*

(Net Blotch of Oat)

Oat seed of the variety WW 17064. Dosage 300 ml per 100 kg seed of formulations containing 150 g a.i. per liter.

4. *Ustilago avenae*

(Loose Smut of Oat)

Oat seed of the variety Sang, infected with 0.75 g of smut spores per liter of water. Dosage 300 ml per 100 kg seed with formulations containing 150 g a.i. per liter.

In the table below the results are, as in Example 9, set out as % control in reference to the comparison with untreated seed in each test for which the percent control is 0.

TABLE

| Fungus | Seed Treating Agent | % Control |
|---|---|---|
| D. Teres | Salt a) | 100 |
| " | Salt (b) | 100 |
| " | Salt (c) | 100 |
| " | Salt (d) | 100 |
| " | Salt (e) | 100 |
| D. graminge | Salt (a) | 97 |
| " | Salt (b) | 95 |
| " | Salt (c) | 97 |
| " | Salt (d) | 97 |
| " | Salt (e) | 98 |
| D. avenae | Salt (a) | 99 |
| " | Salt (b) | 97 |
| " | Salt (c) | 99 |
| " | Salt (d) | 99 |
| " | Salt (e) | 100 |
| U. avenae | Salt (a) | 79 |
| " | Salt (b) | 78 |
| " | Salt (c) | 82 |
| " | Salt (d) | 83 |
| " | Salt (e) | 81 |

We claim:

1. A method for controlling phytopathogenic fungi which method comprises applying to infected or infectable seed or foliage a fungicidally effective amount of an aminoalkanephosphonic acid of the formula

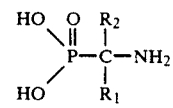

wherein $R_1$ is an alkyl group having 1 to 12 carbon atoms and $R_2$ is hydrogen or an alkyl group having 1 to 12 carbon atoms, or fungicidially effective salts or acid addition salts of the aminoalkanephosphonic acids.

2. A method according to claim 1, wherein $R_2$ is hydrogen.

3. A method according to claim 1, wherein the compounds are used as seed-treating agents.

4. A method for controlling phytopathogenic fungi according to claim 1, wherein 1-aminopropanephosphonic acid, or fungicidally effective salts or acid addition salts of 1-aminopropanephosphonic acid, are used.

5. A method according to claim 4, wherein the compounds are used as seed-treating agents.

6. A method according to claim 1, wherein $R_1$ is an alkyl group having 1 to 5 carbon atoms.

7. A method for controlling phytopathogenic fungi, which method comprises applying to infected or infectable seed as a seed dressing agent or to infected or infectable foliage as foliar spray a fungicidally effective amount of an aminoalkanephosphonic acid of the formula

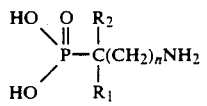

wherein n is 0 or 1, $R_1$ is an alkyl group having 1 to 12 carbon atoms, and $R_2$ is hydrogen or an alkyl group having 1 to 12 carbon atoms, and wherein when n is 1, $R_2$ is hydrogen, or fungicidally effective salts of the aminoalkanephosphonic acids.

8. A method according to claim 7, wherein $R_2$ is hydrogen.

9. A method according to claim 7, wherein $R_1$ is an alkyl group having 1 to 5 carbon atoms.

10. A method according to claim 7, wherein the compounds are used as seed-treating agents.

11. A method for controlling phytopathogenic fungi which method comprises applying to infected or infectable seed as a seed dressing agent or to infected or infectable foliage a fungicidally effective amount of an aminoalkanephosphonic acid of the formula

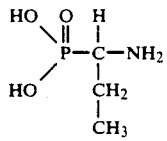

or fungicidally effective salts of this aminopropanephosphonic acid.

12. A method for controlling phytopathogenic fungi according to claim 11, wherein the salt of the aminopropanephosphonic acid is the potassium salt.

13. A method for controlling phytopathogenic fungi according to claim 11, wherein the compounds are used as seed-dressing agents.

14. A method for controlling phytopathogenic fungi according to claim 12, wherein the compounds are used as seed-dressing agents.

15. A method for controlling phytopathogenic fungi on a cereal selected from wheat, barley and oat, which method comprises applying to seed as a seed dressing agent or to foliage of said cereal a fungicidally effective amount of an aminoalkanephosphonic acid of the formula

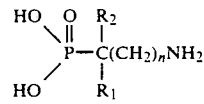

wherein n is 0 or 1, $R_1$ is an alkyl group having 1 to 12 carbon atoms, and $R_2$ is hydrogen or an alkyl group having 1 to 12 carbon atoms, and wherein when n is 1, $R_2$ is hydrogen, or fungicidally effective salts of the aminoalkanephosphonic acids.

16. A method according to claim 15, wherein $R_2$ is hydrogen.

17. A method according to claim 15, wherein $R_1$ is an alkyl group having 1 to 5 carbon atoms.

18. A method according to claim 15, wherein the compounds are used as seed-dressing agents.

19. A method for controlling phytopathogenic fungi on a cereal selected from wheat, barley and oat, which method comprises applying to seed as a seed-dressing agent or to foliage of said cereal a fungicidally effective amount of an aminoalkanephosphonic acid of the formula

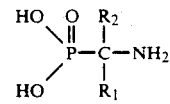

wherein $R_1$ is an alkyl group having 1 to 12 carbon atoms and $R_2$ is hydrogen or an alkyl group having 1 to 12 carbon atoms, or fungicidally effective salts of the aminoalkanephosphonic acids.

20. A method according to claim 19, wherein $R_2$ is hydrogen.

21. A method according to claim 19, wherein $R_1$ is an alkyl group having 1 to 5 carbon atoms.

22. A method for controlling phytopathogenic fungi according to claim 19, wherein the compounds are used as seed-dressing agents.

23. A method according to claim 19, wherein 1-aminopropanephosphonic acid, or fungicide effective salts of 1-aminopropanephosphonic acid, are used.

24. A method according to claim 23, wherein the compounds are used as seed-treating agents.

* * * * *